United States Patent [19]

Taylor et al.

[11] Patent Number: 5,001,048
[45] Date of Patent: Mar. 19, 1991

[54] ELECTRICAL BIOSENSOR CONTAINING A BIOLOGICAL RECEPTOR IMMOBILIZED AND STABILIZED IN A PROTEIN FILM

[75] Inventors: Richard F. Taylor, Boxford; Ingrid G. Marenchic, Walpole; Edward J. Cook, South Hamilton, all of Mass.

[73] Assignee: Aurthur D. Little, Inc., Cambridge, Mass.

[21] Appl. No.: 58,389

[22] Filed: Jun. 5, 1987

[51] Int. Cl.$^5$ .................. C12Q 1/00; C12N 11/02; G01N 33/544; C12M 1/40
[52] U.S. Cl. .................. 435/4; 204/403; 435/20; 435/177; 435/288; 435/817; 436/528; 436/151; 436/806; 530/812
[58] Field of Search ............... 435/4, 20, 177, 181, 435/817, 288; 436/151, 528; 204/403, 418; 530/812

[56] References Cited

U.S. PATENT DOCUMENTS

| | | | |
|---|---|---|---|
| H201 | 1/1987 | Yager | 436/151 |
| 3,833,894 | 9/1974 | Aviram et al. | 340/173 R |
| 4,004,979 | 1/1977 | Arrameas et al. | 435/181 X |
| 4,078,049 | 3/1978 | Felix et al. | 424/1 |
| 4,229,537 | 10/1980 | Hodgins et al. | 435/177 |
| 4,298,685 | 11/1981 | Parikh et al. | 435/7 |
| 4,307,195 | 12/1981 | Karasawa et al. | 435/288 |
| 4,324,858 | 4/1982 | Goodson et al. | 435/20 |
| 4,344,438 | 8/1982 | Schultz | 128/634 |
| 4,352,884 | 10/1982 | Nakashimet et al. | 435/180 |
| 4,357,142 | 11/1982 | Schall et al. | 23/230 B |
| 4,367,072 | 1/1983 | Vogtle et al. | 436/501 |
| 4,371,612 | 2/1983 | Matsumoto et al. | 435/44 |
| 4,415,666 | 11/1983 | D'Orazio et al. | 435/179 |
| 4,418,148 | 11/1983 | Oberhardt | 435/179 |
| 4,456,522 | 6/1984 | Blackburn | 204/416 |
| 4,476,005 | 10/1984 | Tokinaga et al. | 435/817 X |
| 4,484,987 | 11/1984 | Gough | 204/418 |
| 4,490,216 | 12/1984 | McConnell | 435/817 X |
| 4,518,527 | 5/1985 | Numa et al. | 260/112.5 R |
| 4,592,894 | 6/1986 | Panitz | 422/69 |
| 4,637,861 | 1/1987 | Krull | 204/1 T |
| 4,659,665 | 4/1987 | Freeman et al. | 435/817 X |
| 4,661,235 | 4/1987 | Krull et al. | 435/817 X |
| 4,721,601 | 1/1988 | Wrighton | 422/68 |
| 4,839,017 | 6/1989 | Taniguchi et al. | 204/403 |

FOREIGN PATENT DOCUMENTS

| | | |
|---|---|---|
| WO84/03945 | 10/1984 | PCT Int'l Appl. . |
| WO87/03095 | 5/1987 | PCT Int'l Appl. . |
| 1318815 | 5/1973 | United Kingdom . |
| 2136130A | 9/1984 | United Kingdom . |

OTHER PUBLICATIONS

Vadgama, P., *J. Med. Engineer. and Technol.*, 5:293–298, 1981.
88:132789—Chem. Abstracts—1978—T. M. Cahn.
107:191092—Chem. Abstracts—M. Gotoh et al.

*Primary Examiner*—David M. Naff
*Attorney, Agent, or Firm*—Hamilton, Brook, Smith & Reynolds

[57] ABSTRACT

An electrical biosensor for analyte determination is prepared by polymerization of a mixture of a biological receptor capable of binding an analyte in a sample, a protein and a polymerizing agent such as glutaraldehyde to form a polymeric film on a transducer. The mixture preferably contains a stabilizer selected from lipids, detergents and antioxidents. The receptor may be an acetylcholine receptor and the analyte, acetylcholine. A preferred stabilizer is a combination of phosphatidyl choline and octyphenoxypolyethoxyethanol. In carrying out a determination, analyte in a sample binds to the receptor causing a change in an electrical characteristic of the film which is indicative of the presence of the analyte. The biosensor may contain a second polymeric film that is free of the receptor and which serves as a control.

15 Claims, 5 Drawing Sheets

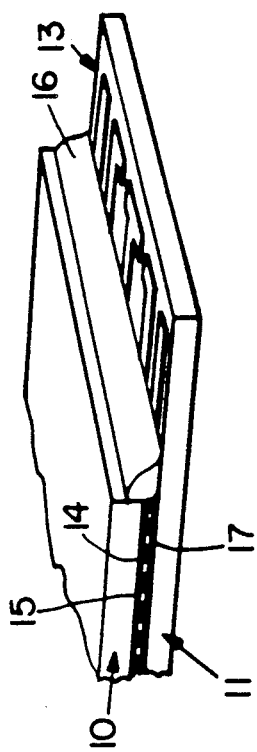
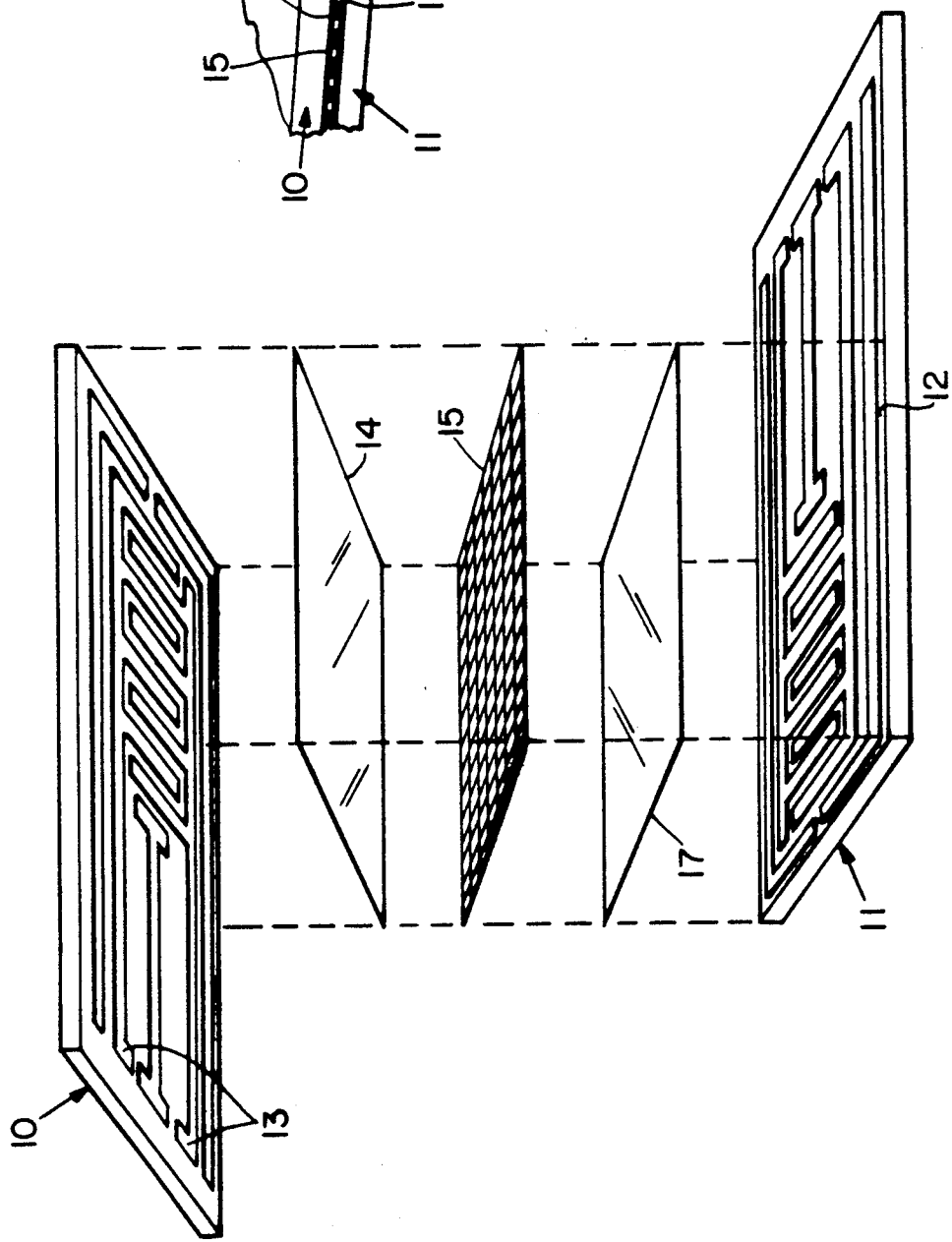

Fig. 6

ELECTRICAL BIOSENSOR CONTAINING A BIOLOGICAL RECEPTOR IMMOBILIZED AND STABILIZED IN A PROTEIN FILM

INTRODUCTION

Biosensors are electronic devices which produce electronic signals as the result of biological interactions. Basically, a biosensor includes a biological receptor linked to an electronic transducer in such a way that biochemical activity is converted into electrical activity. The electronic component of the biosensor measures voltage (potentiometric), current (amperometric), light, sound, temperature, or mass (piezoelectric). Lowe, C. R., Biosensors 1: 3–16(1985). The development of chemical microsensors has fostered the technology necessary for biosensors. For example, an interdigitated gold electrode with a semiconductor film coating has been utilized in measuring concentrations of organic and inorganic vapors. Wohltjen, J., Analytical Chemistry 56:87–103 (1984).

Two types of biosensors are known: enzyme-based or metabolic biosensors and binding or bioaffinity biosensors. Enzymatic or metabolic biosensors use enzymatic or metabolic processes to detect the product of the reaction which occurs between the incoming agent (substrate) and the immobilized receiver (e.g., an enzyme). Enzyme-based biosensors are best exemplified by enzyme electrodes, which are devices which utilize standard electrodes able to detect dissolved gases (such as oxygen) or chemicals (such as urea) electronically. When enzymes attached to the electrodes catalyze a reaction, a gas or chemical is produced. This chemical or gas is detected by a specific electrode, for example, an oxygen or ammonia electrode. Perhaps the best known examples of enzyme electrodes are those which contain glucose oxidase or urease. They can be used to measure, respectively, glucose or urea, as well as to detect end products of multi-enzyme systems (for detection of other substrates). Such enzyme electrodes are well-defined and many are commercially available. Vadgana, P., Journal of Medical Engineering Technology, 5: 293–298 (1981); Solsky, R.6., CRC Critical Review of Analytical Chemistry, 14:1–52 (1983).

Bioaffinity sensors relay on biological binding events for detection of substances of interest. Taylor, R.F., The World Biotech Report 1986, Vol. 2, pp.7–18 (1986). The binding of the environmental substance (ligand) to the immobilized receptor produces a detectable change in the shape or conformation of the receptor and this produces an output signal. Detection of this change can utilize one of a number of methodologies, including optical (interference, refractive index, fluorescence, etc), mechanical (mass or density) or temperature changes.

Until the present time, only antibodies or antigens have been used successfully for bioaffinity sensors. For example, Wasserman antibody in blood has been detected through the use of a membrane containing immobilized antigen. Aizawa, M., et al., Journal of Membrane Science 2:125–132 (1977). Upon interaction of antibody with antigen, a millivolt (mV) change in potential occurs across the membrane; the change is proportional to concentration of antibody present in the blood sample. Antibody-antigen binding is also used in a variety of optically-based biosensors. Place, J. F., et al., Biosensors 1:321–353 (1985). The basic action mechanism in this type of biosensor has not been defined, but appears to be a change in conformation of the immobilized receptor and/or a physical change in the immobilization media (e.g., weight, thickness, light absorbancy, etc.). These changes are detected and amplified electronically using appropriate transducer technology.

There have been attempts to develop other types of binding or bioaffinity sensors. For example, Yager describes a biosensor consisting of a polymerizable lipid bilayer which contains an active membrane protein (e.g., the acetylcholine receptor) and which separates two electrolyte-filled compartments. Synthetic phospholipids in the bilayer membranes are used as stabilizers, and the membrane proteins are incorporated through use of a modification of known methods. Changes in current across the receptor-containing membrane are described as occuring when cholinergic agents are bound and measured using a known (electrode patch) technique. Yager P., U.S. Statutory Invention Registration H201 (Published 1/6/87).

Others have described efforts to immobilize enzymes and other "bioactive" materials onto glass (U.S. Pat. No. 4,357,142) and other surfaces, such as those containing acrylate copolymer (U.S. Pat. No. 4,352,884) or an acrylonitrile polymer (U.S. Pat. No. 4,371,612). See also U.S. Pat. No. 4,307,195; U.S. Pat. No. 4,456,522; U.S. Pat. No. 4,415,666; U.S. Pat. No. 4,418,148; and U.S. Pat. No. 4,484,987.

Although antibody-or antigen- based biosensors are useful in detecting ligands in samples, they have limitations, such as over-selectivity and near irreversible binding, which make it impossible to use them in many instances. Biosensors which are binding sensors or bioaffinity sensors, and which make use of a receptor other than an antibody or an antigen would be very valuable and find use in many contexts in which presently available binding sensors cannot be used.

DISCLOSURE OF THE INVENTION

The present invention relates to receptor-based or bioaffinity sensors and to a method of immobilizing and stabilizing receptors in such sensors. The sensors of the present invention can be used to determine an analyte (or a specific class of analytes) of interest in a liquid or high-water gel. They include a substance referred to as a biological receptor, which binds directly to the analyte of interest; this provides a means of directly detecting and measuring the binding event (between receptor and analyte or class of analyte). The receptor-based biosensor of the present invention can, as a result, be used to detect and to quantitate the analyte of interest. A preferred embodiment utilizes an interdigitated electrode, (contacting the receptor) to measure the impedance of the bound analyte. This measurement yields the concentration of the analyte of interest in the sample being measured. These receptor-based sensors have an important advantage over presently available enzyme-based biosensors, whose function relies on diffusion of a reaction product (i.e., a product of a reaction involving an analyte to be measured) to an electrode at which it is detected.

In one embodiment of the present invention, the biological receptor is the acetylcholine receptor, which is immobilized and stabilized according to the method of the present invention, and used to determine the presence and quantity of acetylcholine or related cholinergic analytes in a sample. In other embodiments of the present invention, the biological receptor can be an antibody, antigen or receptor for hormones, other neural transmitters, vitamins, bacteria, viruses, antibodies and serum lipoproteins. An antibody is a specific receptor for one substance; the other receptors are capable of reacting with more than one substance (i.e., the substance to which they naturally or normally bind and other substances which have similar chemical or physical structures).

Receptor-based biosensors of the present invention provide a means of determining (e.g., detecting and/or quantifying) the presence in a sample of a wide variety of natural and synthetic substances. They are useful in health care, veterinary, agricultural, petrochemical, and pollution monitoring contexts, and are able to provide real-time information about levels of substances of interest or concern. Because of their simplicity and ability to directly measure a binding event which occurs between an appropriately-selected immobilized receptor and ligand (analyte of interest), they present a significant advancement over current detection, monitoring and process control devices.

BRIEF DESCRIPTION OF THE DRAWINGS

FIG. 3A and 3B represent a receptor-based biosensor of the present invention in which a differential (double) chip design is used.

FIG. 6 is a graphic representation of retention of acetylcholine receptor binding activity at room temperature after immobilization in three formulations.

DETAILED DESCRIPTION OF THE INVENTION

Figure 1:
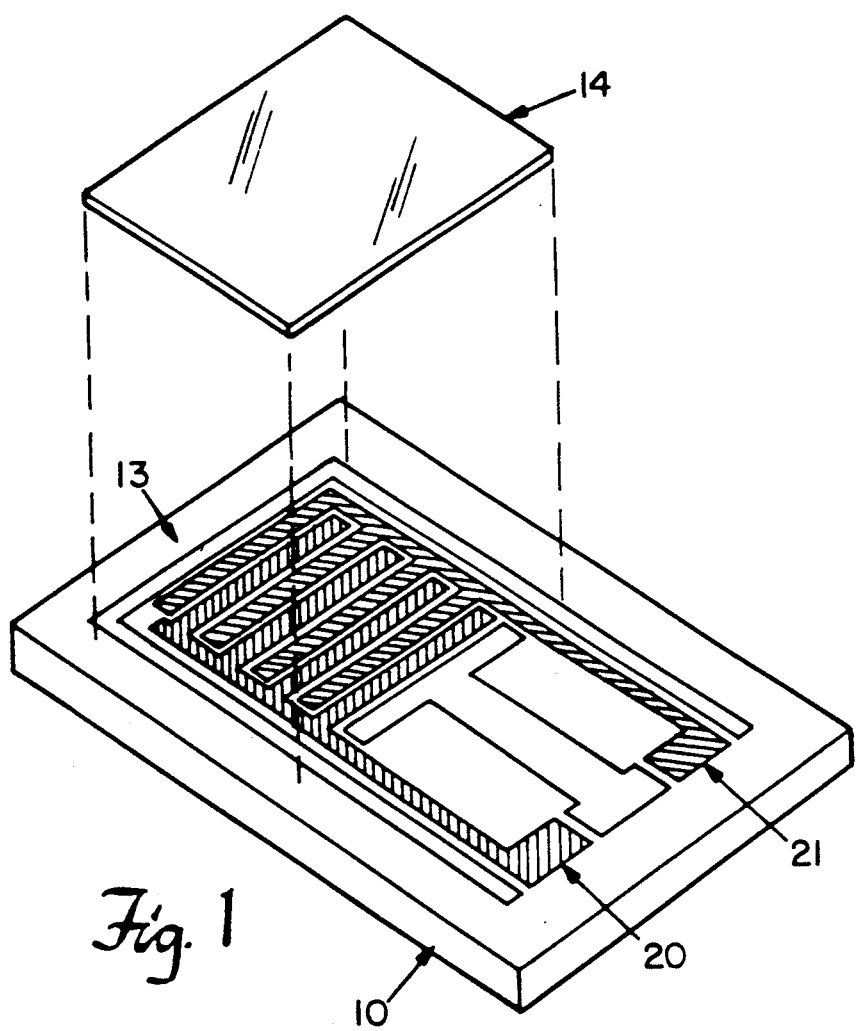
FIG. 1 represents a receptor-based biosensor of the present invention in which a single-chip design is used.

The present invention relates to receptor-based or bioaffinity sensors for the determination of an analyte (or a specific class of analytes) of interest in a sample, and to a method of immobilizing and stabilizing a receptor in the bioaffinity sensor. The receptor-based sensor of the present invention includes a polymeric film in which a receptor selected for its capability to bind an analyte of interest is incorporated.

The receptor-based sensor can be used to determine an analyte of interest in a sample which is a liquid or high-water gel. In addition, it can be used for the determination of an analyte of interest in a gas (e.g., air); in this application, known techniques for transfer of an air sample to a liquid stream are used to provide the liquid to be presented to the sensor.

In the sensor of the present invention, an appropriately selected receptor is immobilized by copolymerization with a base component, such as bovine serum albumin, human serum albumin, acrylic acid, methacrylic acid, collagen or other materials which polymerize. Polymerization can be effected using any means by which it is possible to polymerize the base component and the biological receptor and retain the capability of the biological receptor to bind an analyte of interest. For example, polymerization is effected chemically, such as by addition of a polymerizing catalyst or initiator or a crosslinking agent, such as glutaric dialdehyde (glutaraldehyde), to the receptor and base component combination. Other materials which can be used for this purpose include SPDP, dimethyl suberimidate, disuccinimidyl suberate and bismal bimidonexane. The receptor is selected on the basis of its ability to bind to an analyte of interest to be determined in a sample. As used herein, the term analyte of interest refers to an individual analyte of interest or a specific class (or type) of analyte bound by a receptor.

In one embodiment, a receptor which is an active cell membrane protein is immobilized by being combined with bovine serum albumin and a polymerizing agent or crosslinking agent such as glutaraldehyde. The resulting solution is mixed and cast onto transducers, where it polymerizes as a membrane coat, in which the cell membrane protein is incorporated.

In a specific embodiment in which the receptor is an active cell membrane protein, the neural transmitter acetylcholine receptor is combined with bovine serum albumin (e.g., 99% globulin-free, Sigma Chemical Co.). Glutaric dialdehyde is added to the reaction mixture to effect polymerization. The solution is mixed and cast onto transducers, generally within 5 to 20 minutes after glutaraldehyde addition. This results in formation of a membrane coat (through polymerization) on the transducers. It is allowed to age on the transducers prior to use; aging generally continues for 16–24 hours prior to use. In a further embodiment, one or more materials are added to the solution to stabilize acetylcholine receptor activity in the membrane. These additives include, but are not limited to, phosphatidylcholine, alpha-tocopherol, butylatedhydroxyanisole (BHA), cholesteryl palmitate, Triton TM X-100 octylphenoxy polyethoxyethanol, sodium cholate, cetyltrimethylammonium bromide (CTAB), Tween-80# polyoxyethylene (20)sorbitan mono-oleate and Zwittergents TM 3–10 N-decyl-N-N dimethyl-3-ammonio-1-propane sulfonate and 3–08 N-octyl-N-N dimethyl-3-amino-1-propane sulfonate. Addition of combinations of these additives, such as a combination of phosphatidyl choline with Triton TM X-100, sodium cholate or Zwittergents TM, resulted in a marked increase in stability of the acetylcholine receptor, at the time of immobilization and after prolonged storage. For example, incorporation of phosphatidyl choline and Triton TM X-100 into the film increased retention of binding activity of AChR after 50 days at 4° C. by more than 90% (compared to the immobilized AChR with no phosphatidyl choline and Triton TM X-100). That is, after 50 days at 4° C., the AChR without stabilizer had lost 90% of its binding activity, compared with the AChR with stabilizer.

In another instance, the immobilized receptor is an antibody or an antigen and is immobilized in much the same manner as previously described for the cell membrane protein. For example, an antibody such as immunoglobulin G (IgG) is immobilized in the following way: antibody, bovine serum albumin, and a polymerizing agent, such as glutaraldehyde, are combined. The resulting solution is mixed and cast onto transducers, where it polymerizes as a membrane coat. In a specific embodiment, IgG and bovine serum albumin are combined and glutaraldehyde is added to effect polymerization. The solution is mixed and cast onto transducers, on which it polymerizes as a membrane coat, in which the antibody (or antigen) is incorporated. The membrane coat is then aged for sufficient time (e.g., for 16–24 hours) prior to use.

There are many additional types of biological receptors, useful in the receptor-based sensor of the present invention, which can be immobilized and stabilized according to the method of the present invention.

Other biological receptors include those for hormones, neural transmitters other than the acetylcholine receptor (e.g., adrenergic, gamma aminobutyric, serotonergic, dopaminergic), vitamins and other nutrients, bacteria, viruses, serum lipoproteins and antibiotics. These other receptors, unlike a single antibody, can react with more than one substance. Thus, in addition to binding their "natural" ligands (i.e., those to which they are intended to bind or bind in living organisms), these other receptors can bind substances whose chemical or physical structure is similar to the chemical or physical structure of the natural ligands. Such "class" binding is the basis for drug activity and the toxicity of many substances. For example, the acetylcholine receptor (AChR) described above is normally present in animals and acts as a mediator of neural transmission. The acetylcholine receptor is bound in the membrane of nervous tissue cells and, upon interaction with acetylcholine (its natural ligand), changes conformation and initiates a series of membrane ionic charge changes, which, in turn, result in a nerve impulse.

At least two types of other substances can also bind to the acetylcholine receptor: substances which cause changes in the AChR and, ultimately, nerve stimulation and substances which block changes in the AChR conformation and, thus block nerve stimulation. For example, substances such as muscarine, phencyclidines, etc., can cause these conformational changes in the AChR and cause nerve stimulation. Substances such as nicotine, curare and the snake toxin alpha-bungarotoxin, can also bind to the AChR. These substances, however, block the ability of the AChR to change conformation and block nerve stimulation. As a result, an acetylcholine. receptor-based biosensor of the present invention is useful to detect and quantify compounds or substances which act on the receptor. For example, such a biosensor is useful for the determination of organophosphorus compounds (e.g., diisopropylfluorophosphate, soman, sarin, VX) drugs (e.g., succinylcholine, nicotine, decamethonium, pilocarpine, carbachol, physostigmine), naturally-occurring toxins (including alpha bungarotoxin curare; atropine; homarine) and a variety of environmental chemicals and pollutants (e.g., malathion, diazinon, carbaryl). As a result, a sensor of this type can be used to determine such substances in, for example, situations in which chemicals or pesticides are made (e.g. manufacturing plants) or used (e.g., agricultural or farming uses, home gardening uses, defense applications), as well as in situations in which their presence and/or concentrations are monitored (e.g., water supplies, air concentrations). It also has medical applications (e.g., in a clinic, hospital, physicians practice) in determining drugs, viruses, hormones, toxins, etc. in patients.

The following description illustrates the components and function of a biosensor in which the receptor is acetylcholine receptor. However, the same description is possible of a biosensor of the present invention in which different biological receptor is incorporated; the following description is not meant to be limiting in any way.

As described previously, acetylcholine receptor (e.g., $N_2$ nicotinic acetylcholine receptor from *Electrophoris electricus* (eel), partially purified) is combined with a film base (e.g., bovine serum albumin), a polymerization catalyst (e.g., glutaraldehyde) and at least one stabilizer (e.g., phosphatidylcholine or Triton ™ X-100). The resulting solution is cast onto transducers, on which it polymerizes, forming a receptor-containing membrane.

In one embodiment of the present invention, which is represented in FIG. 1, a single-chip design is used, in which the transducer is a quartz or glass substrate 10 containing two-terminal interdigitated gold electrodes 20 and 21. A receptor-containing membrane 14 is contacting the interdigitated area of the gold electrodes and, in this instance, is an acetylcholine receptor membrane. An alternating current field across the electrodes is used to detect binding of substances (analyte of interest) to the immobilized receptors. For example, when the biosensor contains immobilized acetylcholine receptor and a ligand (analyte of interest), such as acetylcholine or alpha-bungarotoxin, is present in a sample being analyzed, binding of the receptor and the analyte of interest occurs, producing changes in the alternating current impedance of the biosensor. The changes are directly proportional to the concentration of the ligand of interest to which the biosensor is exposed (e.g., by contact with a sample). Similarly, when human immunoglobulin G is the receptor included in the biosensor and antibody to it is present in a sample being tested, changes in the alternating current impedance of the biosensor occur and are directly proportional to the concentration of ligand (i.e., antibody to immunoglobulin G) present. In both cases, a fixed frequency of, for example, 120 Hz or 1 kHz and a fast-responding digital LCR meter are used.

In one embodiment of the biosensor of the present invention, a double chip design is used. This double biosensor includes a non-receptor (control) membrane and a receptor-containing membrane. The control membrane serves as a detector for background, nonspecific binding to the membranes. Any signal from such binding to the control membrane is subtracted from the signal resulting from the receptor-containing membrane. As a result only signal related to specific ligand-receptor binding is reported.

FIGS. 3A and 3B illustrates the double biosensor apparatus with its various components. A conductor 13 is evaporated through a mask to form an interdigitated pattern on each substrate 10 and 11. In a preferred embodiment, gold is evaporated onto each silicon dioxide substrate, 10 and 11, forming a 1–2 micron layer. A bonding agent 12 (typically Mg, Ti, or Zr) is used to insure good adhesion of the gold to the $SiO_2$ substrate. The biological receptor containing membrane 14 chosen for a particular embodiment is then formed on the interdigitated section of one conductor. The receptor surface of membrane 14 associated with substrate 10, for example, is then positioned face to face with a non-receptor containing reference membrane 17 associated with substrate 11. An equipotential barrier 15 is interposed between the receptor surface 14 and membrane 17. The barrier 15 serves to inhibit current flow between the two membrane surfaces and may be comprised of an insulator or a suitably biased conductor. Seal 16 defines and seals a volume between the membrane surfaces. This volume is filled with material to be analyzed, or alternatively, placed in a fluid stream that is being analyzed. The present invention allows the sampling of very small volumes of a process stream while retaining high sensitivity to variations in the spatial or temporal changes in the concentration of the material being analyzed. Traditional microfabrication techniques may be used in making these microsensors.

Figure 4:
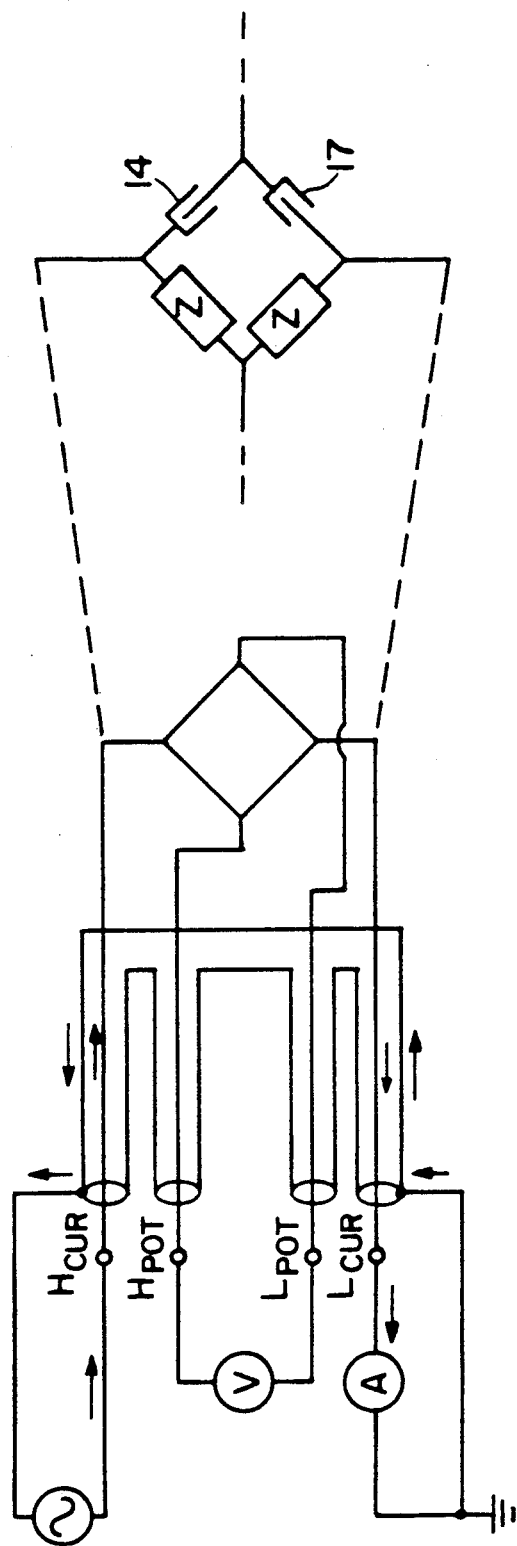
FIG. 4 is a graphic representation of a differential (double) chip test circuit.

FIG. 4 shows a standard bridge circuit for measuring the impedence across the receptor membrane 14. The impedance of the reference membrane must be large with respect to the receptor membrane, but small with respect to the impedance of the instrumentation. This differential measurement yields ½ of the difference in the impedance between the reference membrane and the receptor membrane.

Such a biosensor would be useful to detect and measure ligand concentrations in clinical settings (e.g., blood and urine samples), in environmental and industrial settings (air and water) and in industrial process streams (e.g., fermentation broths and chemical syntheses solutions).

Receptors can bind a range or class of substances which have similar structures and physiological activity. Because receptors can also distinguish whether a substance will stimulate or block the receptor-mediated physiological response, they represent sophisticated detectors for chemicals such as therapeutic and abused drugs, insecticides, toxic agents, hormones, etc. Examples of known receptors include neural receptors, such as cholinergic, adrenergic, gamma aminobutyric, serotonergic, and dopaminergic receptors; hormonal receptors such as opiate, steroid, and insulin receptors; nutrient receptors, such as cholesterol and vitamin receptors; and cell surface receptors, such as lectin, viral, antibiotic and low density lipoprotein (LDL) receptors. Additionally, plants contain specific receptors for growth hormones (and related toxins), such as auxin, cytokinins and indoleacetic acid.

The subject invention will now be illustrated by the following examples, which are not to be seen as limiting in any way.

Example 1 Receptor Preparation

Acetycholine receptors to be used in the biosensor of the present invention were prepared according to the method below, which is a modification of methods described by Klett et al. and Karlin et al. Klett, R. P. et al., *Journal of Biological and Chemistry*, 248:6841-6853, (1973); Karlin, A. et al., *Methods in Receptor Research* (Belcher, M., ed), p. 1-35 (1976).

Approximately 50 g of minced electric organ tissue from the electric eel (*Electrophorus electricus*) was homogenized in 150 ml of 1 mM EDTA pH 7.4, for 1 min. The homogenate was filtered through cheesecloth to remove solid matter, and the filtrate was centrifuged at 20,000 ×g for 15 min at 4° C. The resulting pellet was homogenized for 30 sec in 100 ml of 50 mM $Na_2$—$KH_2PO_4$ buffer, pH 7.4, containing 0.02% sodium azide and centrifuged again at 20,000×g for 15 min at 4° C. The resulting pellet was homogenized for 30 sec in 20 ml of 10 mM $Na_2$—$NaH_2PO_4$ buffer, pH 8, containing 50 mM NaCl, (mM EDTA and 3% Triton TM X-100). The homogenate was gently stirred at room temperature for 60 min and then centrifuged at 100,000×g for 60 min at 4° C. The resulting supernatant was adjusted to pH 7.4 with 0.6 M $Na_2HPO_4$, and approximately 10 ml was applied to a 1.5×40cm column of Sephadex TM G-50 (Pharmacia, Piscataway, NJ). The column was equilibrated and eluted with 0.02 M $Na_2HPO_4$—$KH_2PO_4$ buffer, pH 6.8, containing 2% Triton TM X-100. The acetylcholine receptor elutes from the column in approximately 3 to 10 ml (void volume). This is hereafter referred to as the acetylcholine receptor (AChR).

The activity of the AChR was determined using the standard DEAE-filter disc binding assay. This method utilizes the binding of [$^{125}I$] alpha-bungarotoxin to determine AChR content in preparations. Schmidt, J. and M. J. Raftery, *Analytical Biochemistry*, 52:249-354 (1973).

Example 2 Immobilization Formulations

The membrane formulation (basic membrane formulation) used for immobilization of both receptor and antibody included 300 mg of Bovine Serum Albumin (BSA, 99% globulin-free, Sigma Chemical Co., St. Louis, Mo.) in 0.02 M $K_2HPO_4$ buffer (pH 6.8) containing 0.1% Triton TM X-100. In the case of the AChR-based sensor, the BSA was in 4 ml of the buffer and 1 ml of AChR preparation was included in the basic membrane formulation. A coating solution which included approximately 2% (by weight) receptor preparation or approximately 0.5% AChR (by weight) was used. On a per sensor basis, this represents approximately 10 ug (micrograms) of receptor preparation (see Example 1) or approximately 1-2 ug AChR. Sensors containing a wide range of levels of AChR (e.g. 0.1 ug to more than 100 ug) can be used. From 0.1 to 5% (by volume) of glutaric dialdehyde (glutaraldehyde) was added to the reaction mixture to effect polymerization. The solution was mixed and cast onto transducers within 5 to 20 min after glutaraldehyde addition. The solution polymerized as a membrane coat on the transducer within 15 to 45 min. It was allowed to age on the transducer for 16-24 hr prior to use.

In the case of antibody-containing membranes, up to 75 mg of antibody or antigen is added to 300 mg of BSA in 5 ml of the buffer described above. This is equivalent to coatings containing approximately 25% (by weight) IgG on a per sensor basis, which is approximately 250 to 500 ug of IgG per chip. Sensors containing a wide range of levels of IgG (e.g., 1 ug to 1000 ug) can be used. Glutaraldehyde is added for polymerization, and the resulting solution treated as described for the AChR-based sensor.

Selected materials were added to the basic membrane formulation to assess their ability to stabilize AChR activity in the membrane. These included phosphatidylcholine, alpha-tocopherol, butylatedhydroxyanisole (BHA), cholesteryl palmitate, Triton TM X-100, sodium cholate, cetyltrimethylammonium bromide (CTAB) Tween-80 TM, and Zwittergents 3-10 and 3-08. Varying concentrations of 0.1 to 5% by weight of combinations of these stabilizing agents were shown to markedly stabilize AChR activity immediately upon immobilization and after prolonged storage.

Table 1 summarizes the concentrations of each stabilizer tested in the membrane formulations. Individually, each stabilizer, when added to the basic membrane formulation into which AChR had been incorporated increased AChR stability (in comparison to non-stabilized membranes).

TABLE 1

| Stabilizers Added to Receptor Membranes | |
|---|---|
| Stabilizer | Amount |
| Sodium cholate | |
| CTAB | |
| Zwittergent TM 3-10 | 0.1 to 5% by volume |
| Zwittergent TM 3-08 | |
| Triton TM X-100 | |
| Tween TM 80 | |
| Phosphatidylcholine | 0.1 to 10% by weight |

TABLE 1-continued

| Stabilizers Added to Receptor Membranes | |
|---|---|
| Stabilizer | Amount |
| alpha-Tocopherol | 0.1 to 5% by weight |
| BHA | 0.001 to 1% by weight |
| Cholesteryl esters (e.g., palmitate) | 0.1 to 10% by weight |

Such stabilization was measured as retention of binding activity after immobilization after storage for at least 2 days at room temperature. Table 2 shows results of one set of experiments in which varying concentrations of detergents as stabilizers were used. As is shown by these data, Triton TM X-100 and sodium cholate were found to be the best stabilizing detergents.

TABLE 2

| Effect of Detergent Stabilizers on AChR Membrane Activity[a] | | |
|---|---|---|
| Detergent | % By Volume | % Activity Increase[b] |
| Triton TM X-100 | 0.1 | 12 |
| | 0.5 | 55 |
| | 1.0 | 85 |
| | 2.0 | 110 |
| Sodium cholate | 0.5 | 18 |
| | 1.0 | 110 |
| | 2.0 | 145 |
| Zwittergent TM 3-08 | 0.5 | 0 |
| | 1.0 | 55 |
| | 2.0 | 55 |
| Zwittergent TM 3-08 | 0.5 | 20 |
| | 1.0 | 30 |
| | 2.0 | 38 |
| CTAB | 0.5 | 4 |
| | 1.0 | 18 |
| | 2.0 | 28 |

[a]24 to 48 hours after immobilization
[b]Over non-detergent containing membrane. Typically, such control membranes retain 20-30% AChR activity after immobilization.

Combinations of stabilizing agents were also tried. Results of these studies are shown in Table 3. The best of the combinations tested included detergent plus phosphatidylcholine.

TABLE 3

| Effect of Detergents Plus Phosphatidyl Choline and BHA on AChR Membrane Activity[a] | | | |
|---|---|---|---|
| Detergent | % By Volume | Other Agent | % By Volume | % Activity Increase |
| Triton TM X-100 | 0.5 | PC | 0.6 | −50 |
| | 2.0 | PC | 0.6 | 145 |
| Sodium Cholate | 0.5 | PC | 0.6 | 85 |
| | 2.0 | PC | 0.6 | 285 |
| Zwittergent TM 3-10 | 2.0 | PC | 0.6 | 126 |
| | 2.0 | PC | 1.5 | 129 |
| | 2.0 | PC | 3.0 | 122 |
| | 2.0 | BHA | 0.003 | 87 |
| | 2.0 | BHA | 0.006 | 13 |
| | 2.0 | BHA | 0.03 | 13 |

[a,b]See Footnotes Table 2.

Figure 5:
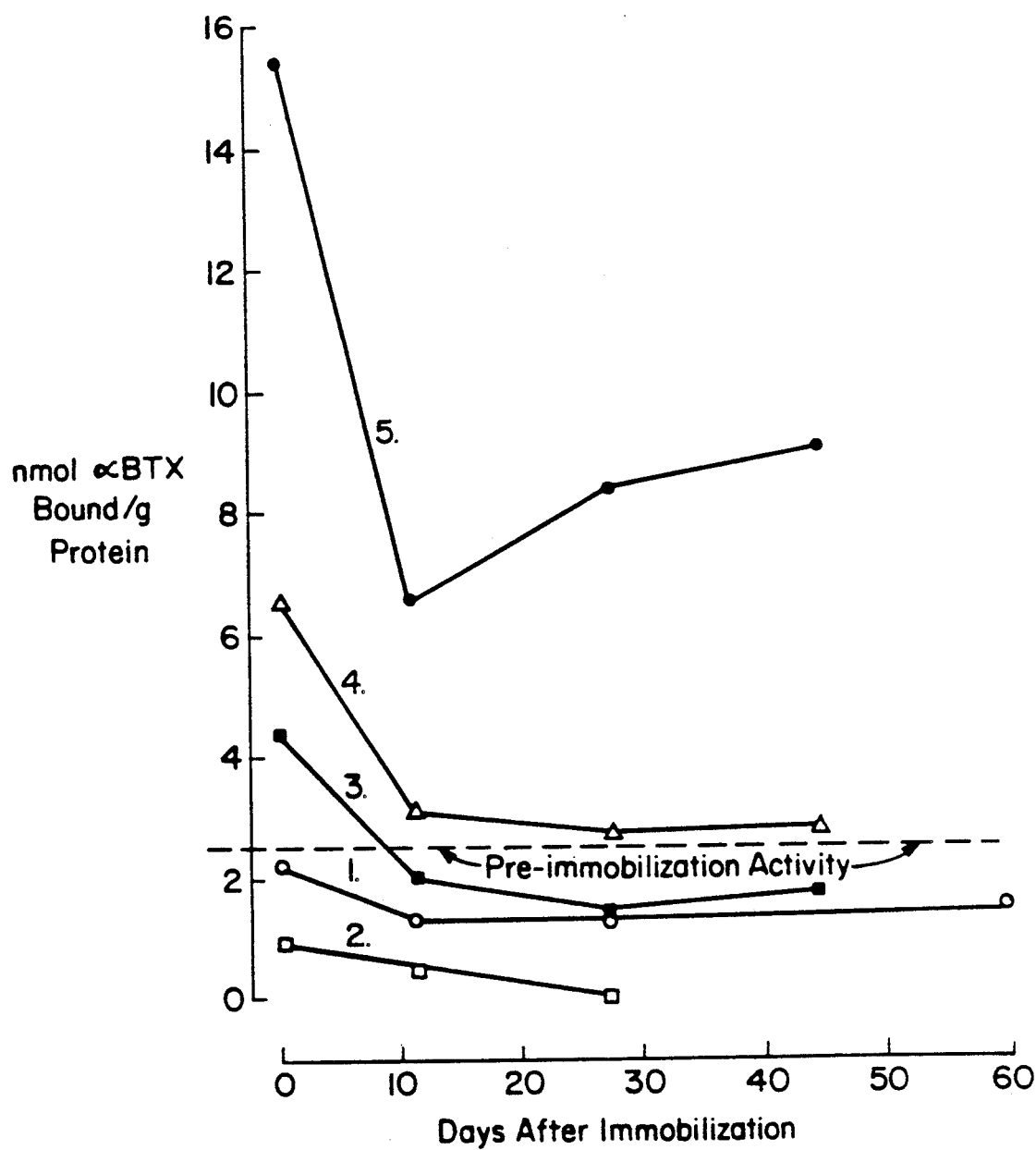
FIG. 5 is a graphic representation of retention of acetylcholine receptor binding activity at 4° C., after immobilization in five formulations.
Figure 6:
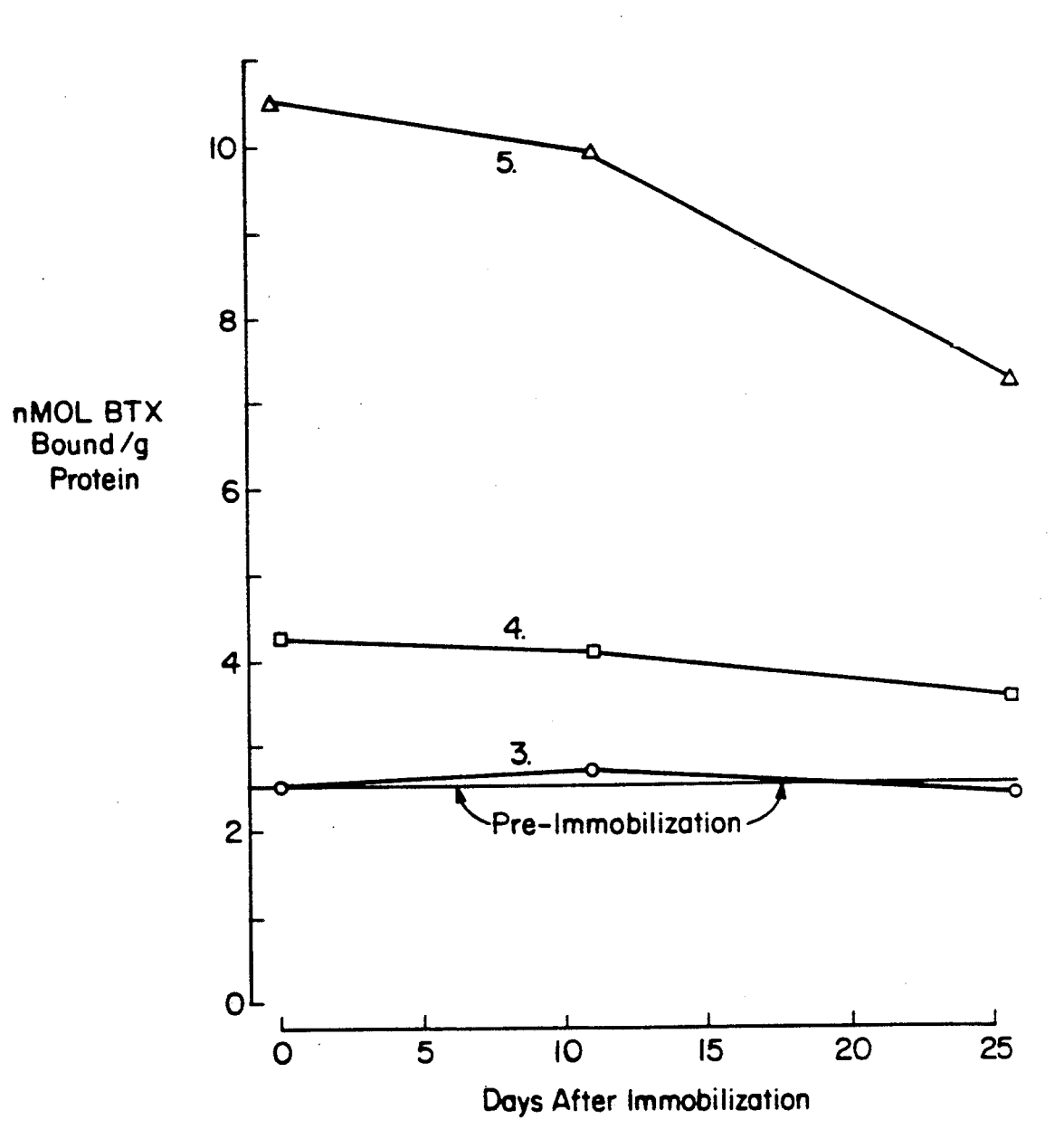

FIG. 5 is a graphic representation of activity retention (measured as binding of alpha-bungarotoxin) over time for a number of formulations. At 4° C., the most stable membranes were those containing Zwittergent 3-10 or sodium cholate, in combination with phosphatidylcholine. At room temperature, the most stable membranes over time were those containing Zwittergent TM 3-10 and phosphatidylcholine, sodium cholate and phosphatidylcholine or TX-100 and phosphatidylcholine, as shown in FIG. 6.

Detergent was shown not to affect antigen binding activity. This demonstrated that antibody-containing membranes can be prepared with or without addition of stabilizers.

A screening method was used to cast the receptor or antibody-containing membrane mixture over the electrode surface to a reproducible thickness which varied, for example, from 1 to 50 micron (±10-15%), as measured by ellipsometry.

Example 3 Analyte Measurements

All measurements utilized wetted biosensors (i.e., sensors presoaked in deionized water and test buffer). The biosensor was washed with deionized water to a constant output value (that is, it maintained the same impedance value upon further washing). This established a baseline value for the sensor in absence of ligand. Test samples in buffer were then added. Output (changes in impedance, etc) was recorded as a function of time.

Figure 2:
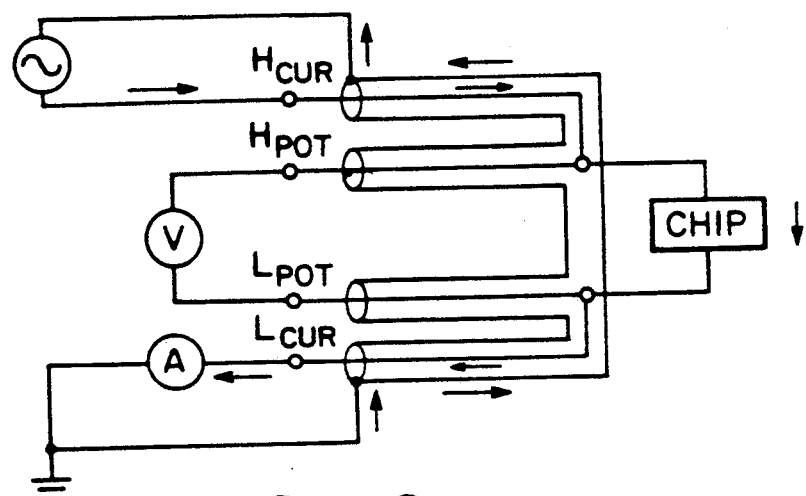
FIG. 2 is a graphic representation of a single chip test circuit.

Two approaches were used to evaluate the functionality of the two types (i.e., receptor and antibody-based) of biosensors. In the first approach, measurements were taken sequentially on control and test sensors ("chips") and compared. This approach can be done quickly for rapid evaluation of a sensor (FIGS. 1 and 3). However, background (i.e., non specific binding to the sensor) is not subtracted out automatically. A second configuration, as shown in FIGS. 2 and 4, which utilizes a sensor incorporating both a reference (control) and a test membrane ("double membrane chips") was also used. This allows for simultaneous challenge (i.e., challenge of both the control and the receptor-containing biosensor at the same time) and background is automatically subtracted out.

In the case in which sequential measurements were used, alternating current measurements were made on the sensors, and changes were recorded in impedance (measured in ohms), capacitance or phase angle. Samples in volumes of 5 to 200 microliters (ul) were analyzed; concentrations in such solutions were approximately 0.1 to 500 micrograms/ml (ug/ml).

Typically, a sample to be tested (i.e., one thought to contain an analyte of interest) was applied to a sensor which had been previously equilibrated with deionized water and readings of output impedance from the sensor were taken. Equilibration to constant readings occurred within 2 to 10 sec. Readings remained stable for at least the 5 minutes during which the output was routinely monitored. The sensor was then washed with deionized water to background equilibrium, sample was again added and readings were taken. In each case 2 to 5 cycles were carried out in this way.

Results showed that in the case of reversibly binding analytes of interest, (such as acetylcholine (ACh) for the AChR), analyte can be quickly washed out of the sensor and the sensor will then, reproducibly, re-react with the analyte. As shown in Table 4, in one series with ACh and an AChR sensor, repeated applications (after washing) on the same sensor with ACh solutions of the same concentration resulted in less than 3% variation among readings.

TABLE 4

| Reproducibility of Test Data With Sequential Addition of Test Agent[a] | | | |
|---|---|---|---|
| | KΩ | | |
| Step[b] | Test 1[c] | Test 2 | Test 3 |
| Background | 240.0 | 247.0 | 243.0 |
| Add Sample | 26.5 | 27.2 | 17.4 |

TABLE 4-continued

Reproducibility of Test Data With Sequential Addition of Test Agent[a]

| Step[b] | KΩ | | |
|---|---|---|---|
| | Test 1[c] | Test 2 | Test 3 |
| Wash | 236.0 | 250.0 | 247.0 |
| Add Sample | 27.1 | 29.5 | 16.7 |
| Wash | 230.0 | 245.0 | 247.0 |

[a] Using an AChR sensor and ACh as the test agent.
[b] Each step reached equilibrium within 1 min.
[c] Test samples were 50 to 100 ul of solutions of ACh at concentrations: 1, 500 ug/ml; 2, 50 ug/ml; 3, 5 ug/ml.

The same was shown to be true of all other AChR sensors tested. Additionally, in the dose-response experiments described below, in which a single sensor was used in assessing device-to-device variability, results showed that a single sensor can be recycled at least 24 times with no apparent performance decrement.

Table 5 shows data from an assessment of dose-response to analytes of interest and a control substance (glucose) by the AChR sensor. Of particular interest in this table is the percentage change in resistance evident between control and AChR sensors. Glucose, which does not bind to the AChR, showed no change when applied to either sensor. ACh, the natural binding material for the AChR, showed a dose-dependent change in resistance which reached a change of over 100% at the highest concentration tests. Alpha-bungarotoxin (alpha-BTX) shows a similar dose response. Thus, the AChR sensor detects specific binding substances in a dose-dependent manner.

TABLE 5

Response of Control and AChR Sensors to Agent Challenge[a]

| Sensor[b] | Glucose | | | ACh | | | alphaBTX | | |
|---|---|---|---|---|---|---|---|---|---|
| | Conc.[c] | KΩ | % Change[d] | Conc. | KΩ | % Change | Conc. | KΩ | % Change |
| Control | 0.5 | 28 | — | — | — | — | — | — | — |
| | 5.0 | 33 | — | 5 | 23 | — | 5 | 42 | — |
| | 50.0 | 33 | — | 50 | 11 | — | 50 | 23 | — |
| | 500.0 | 58 | — | 500 | 4 | — | 500 | 13 | — |
| AChR | 0.5 | 29 | 3 | — | — | — | — | — | — |
| | 5.0 | 33 | 0 | 5 | 25 | 8 | 5 | 42 | 0 |
| | 50.0 | 35 | 6 | 50 | 17 | 55 | 50 | 34 | 48 |
| | 500.0 | 61 | 5 | 500 | 9 | 125 | 500 | 27 | 108 |

[a] Using an AChR sensor with ACh and alpha BTX as agents and glucose as a control (non-binding) agent.
[b] Control sensor is the same formulation as AChR but with no AChR added.
[c] From 50 to 100 uL of sample was applied per test. All tests in duplicate. Concentrations in ug/ml.
[d] With respect to control.

Table 6 shows results of an assessment of biosensors in which the receptor is immobilized human IgG. Challenge of the sensors with antibody to IgG (alphaIgG) resulted in significant resistance changes. Thus, the technology is also applicable to antibody-based biosensors.

TABLE 6

Response of Control and IgG Sensors to Challenge by alphaIgG[a]

| Sensor[b] | Response (KΩ) | % Change[c] |
|---|---|---|
| Control | | |
| #1 | 136 | — |
| #2 | 86 | — |
| IgG | | |
| #1 | 280 | +105% |
| #2 | 248 | +188% |

[a] AC impedance measurements at 120 Hz using deionized water as the electrolyte. Challenge was with antibody to IgG (alpha IgG) using a 10 uL test solution volume containing approximately 500–700 ug alpha IgG.
[b] Control sensor differs only in that it does not contain IgG. The IgG sensor membrane contained 25% by weight human IgG.
[c] With respect to control.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A method of immobilizing and stabilizing a biological receptor in a polymeric film on a transducer for the determination of an analyte in a sample, comprising:
   (a) forming a mixture by combining a biological receptor capable of binding the analyte, a base component which is a protein, a polymerizing agent and at least one stabilizer selected from the group consisting of lipids, detergents and antioxidants, under conditions appropriate for polymerization to occur; and
   (b) forming a film by polymerization of the mixture of (a) on a transducer.

2. A method of claim 1 wherein the protein is selected from the group consisting of bovine serum albumin, human serum albumin, gelatin and collagen; the polymerizing agent is glutaraldehyde; the lipid is selected from the group consisting of phosphatidylcholine, and cholesteryl palmitate, the detergent is selected from the group consisting of octylphenoxy polyethoxyethanol, sodium cholate, cetyltrimethylammonium bromide, polyoxyethylene sorbitan monooleate, N-decyl-N-dimethyl-3ammonio-1-propane sulfonate and N-octyl-N-dimethyl-3-ammonio-1-propane sulfonate and the antioxidant is selected from the group consisting of alpha-tocopherol and butylated hydroxyanisole.

3. A method for determining an analyte in a sample comprising:
   (a) contacting the sample with a biosensor comprising:
      (1) a polymeric film formed by chemical copolymerization of a solution comprising:
         (a) a base component which is a protein (b) a biological receptor capable of binding the analyte; and (c) at least one stabilizer selected from the group consisting of lipids, detergents and antioxidants; and (2) a sensor comprising a first conductor and a second conductor which are in contact with the polymeric protein film; and (b) determining a change in an electrical characteristic of the polymeric protein film, whereby a change is indicative of the presence of analyte in the sample.

4. A biological receptor-containing biosensor for the determination of an analyte in a sample, comprising:

(a) a polymeric film formed by chemical copolymerization of a solution comprising (1) a base component which is a protein;

(2) a biological receptor capable of binding the analyte; and (3) at least one stabilizer selected from the group consisting of lipids, detergents and antioxidants;

(b) a first sensor comprising a first conductor and a second conductor which are in contact with said film; and (c) a current source in conductive contact with the first and second conductors for measuring an electrical characteristic of the polymeric film.

5. A biological receptor-containing biosensor of claim 4 wherein the biological receptor is a neurological receptor.

6. A biological receptor-containing biosensor of claim 5 wherein the neurological receptor is an acetylcholine receptor.

7. A biological receptor-containing biosensor of claim 4 wherein the protein is selected from the group consisting of serum albumin, gelatin and collagen.

8. A biological receptor-containing biosensor of claim 4 wherein the lipid is selected from the group consisting of: phosphatidyl choline and cholesteryl palmitate, the detergent is selected from the group consisting of octylphenoxy polyethoxethanol, sodium cholate, cetyltrimethyl-ammonium bromide, polyoxyethylene, sorbitan monooleate, N-decyl-N-dimethyl-3-ammonio-1-propane sulfonate and N-octyl-N-dimethyl-3-ammonio-1- propane sulfoante, and the antioxidant is selected from the group consisting of alpha-tocopherol and butylated hydroxyanisole.

9. An acetylcholine receptor-containing biosensor for the determination of an analyte in a sample comprising:

(a) a polymeric film formed by chemical copolymerization of a solution comprising (1) a base component which is a protein selected from the group consisting of serum albumin, gelatin and collagen;

(2) acetycholine receptor capable of binding the analyte; and (3) at least one stabilizer selected from the group consisting of lipids, detergents and antioxidants;

(b) a first sensor comprising a first conductor and a second conductor which are in contact with said film; and (c) a current source in conductive contact with the first and the second conductors for measuring an impedance of the film.

10. A receptor of claim 9 wherein the stabilizer is a combination of the lipid, phosphatidyl choline, and the detergent, octylphenoxypolyethoxyethanol.

11. A biological receptor-containing biosensor for the determination of an analyte in a sample, comprising a first polymeric film comprising a protein, a stabilizer selected from the group consisting of lipids, detergents and antioxidants and a biological receptor capable of binding the analyte, the first polymeric film being in contact with a first electrical sensor for measuring an electrical characteristics of the first polymeric film and further comprising:

(a) a second polymeric film free of receptor for binding the analyte, the second polymeric film being in contact with a second electrical sensor for measuring an electrical characteristic of the second polymeric film;

(b) a potential barrier interposed between the second polymeric film and the first polymeric film, such that the barrier hinders current flow between said second polymeric film and the first polymeric film;

(c) a current source; and (d) a circuit contacting the current source and the first and the second electrical sensors for measuring absolute and the differential changes in the electrical characteristics of the first and second films.

12. A biological receptor-containing biosensor of claim 11 wherein the biological receptor is a neutrological receptor.

13. A biological receptor-containing biosensor of claim 12 wherein the neurological receptor is an acetylcholine receptor.

14. A biological receptor-containing biosensor of claim 11 wherein the protein is selected from the group consisting of serum albumin, gelatin and collage.

15. A biological receptor-containing biosensor of claim 11 wherein the lipid is selected from the group consisting of: phosphatidyl choline and cholesteryl palmititate, the detergent is selected from the group consisting of octylphenoxypolyethoxethanol, sodium cholate, cetyltrimethyl-ammonium bromice, polyoxyethylene, sorbitan monooleate, N-decyl-N-dimethyl-3-ammonio-1-propane sulfonate and N-octyl-N-dimethyl-3-ammonio-1-propane sulfonate and the antioxidant is selected from the group consisting of alpha-tocopherol and butylated hydroxyanisole.

* * * * *